United States Patent [19]

Young

[11] Patent Number: 4,553,963

[45] Date of Patent: Nov. 19, 1985

[54] ROLLER CLAMP CONTROLLER

[75] Inventor: Harvey T. Young, El Toro, Calif.

[73] Assignee: American Hospital Supply Corp., Evanston, Ill.

[21] Appl. No.: 610,681

[22] Filed: May 16, 1984

[51] Int. Cl.[4] .............................................. A61M 5/00
[52] U.S. Cl. ........................................ 604/246; 251/6; 604/34
[58] Field of Search .............. 604/246, 245, 236, 207, 604/34, 30; 251/6

[56] References Cited

U.S. PATENT DOCUMENTS 3,831,625 8/1974 Roediger .
4,105,028 8/1978 Sadlier et al. .
4,204,538 5/1980 Cannon ................. 604/246
4,207,871 6/1980 Jenkins ................. 604/246
4,262,824 4/1981 Hrynewycz ............. 604/246 X
4,300,552 11/1981 Cannon .
4,397,642 8/1983 Lamadrid .

Primary Examiner—John D. Yasko
Attorney, Agent, or Firm—Gordon L. Peterson

[57] ABSTRACT

An apparatus for administering a fluid from a source to a patient comprising a flexible conduit extending from the source to the patient and a roller clamp, including a rotary member which rotates and translates to restrict the conduit to control the flow of fluid to the patient. The roller clamp is retained in position, and a motor drives the rotary member to the desired position.

20 Claims, 6 Drawing Figures

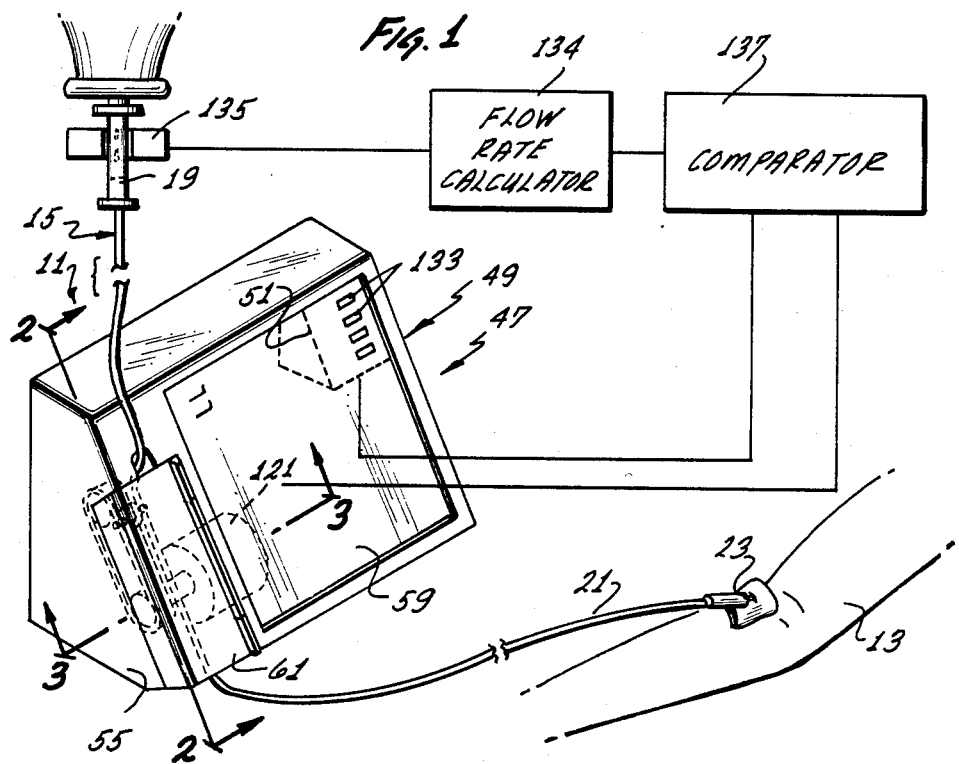
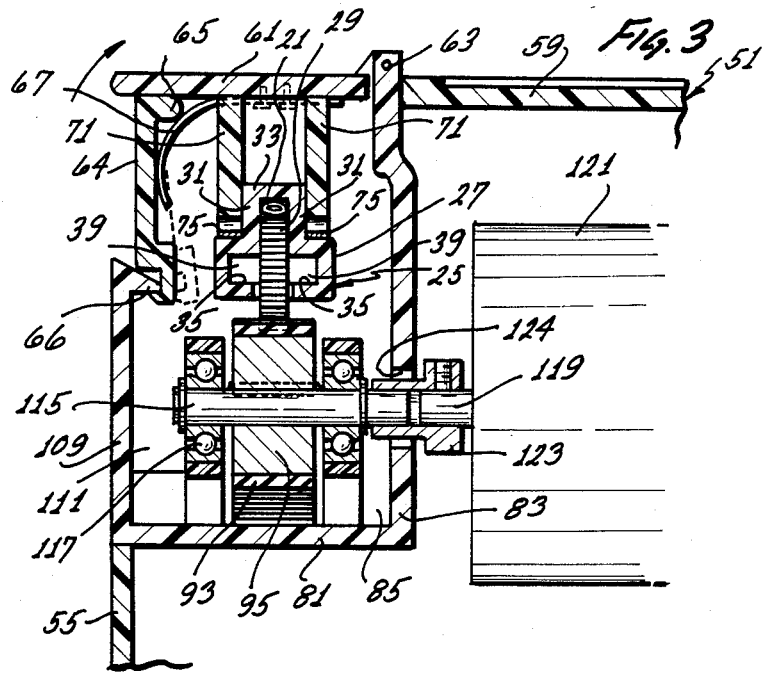

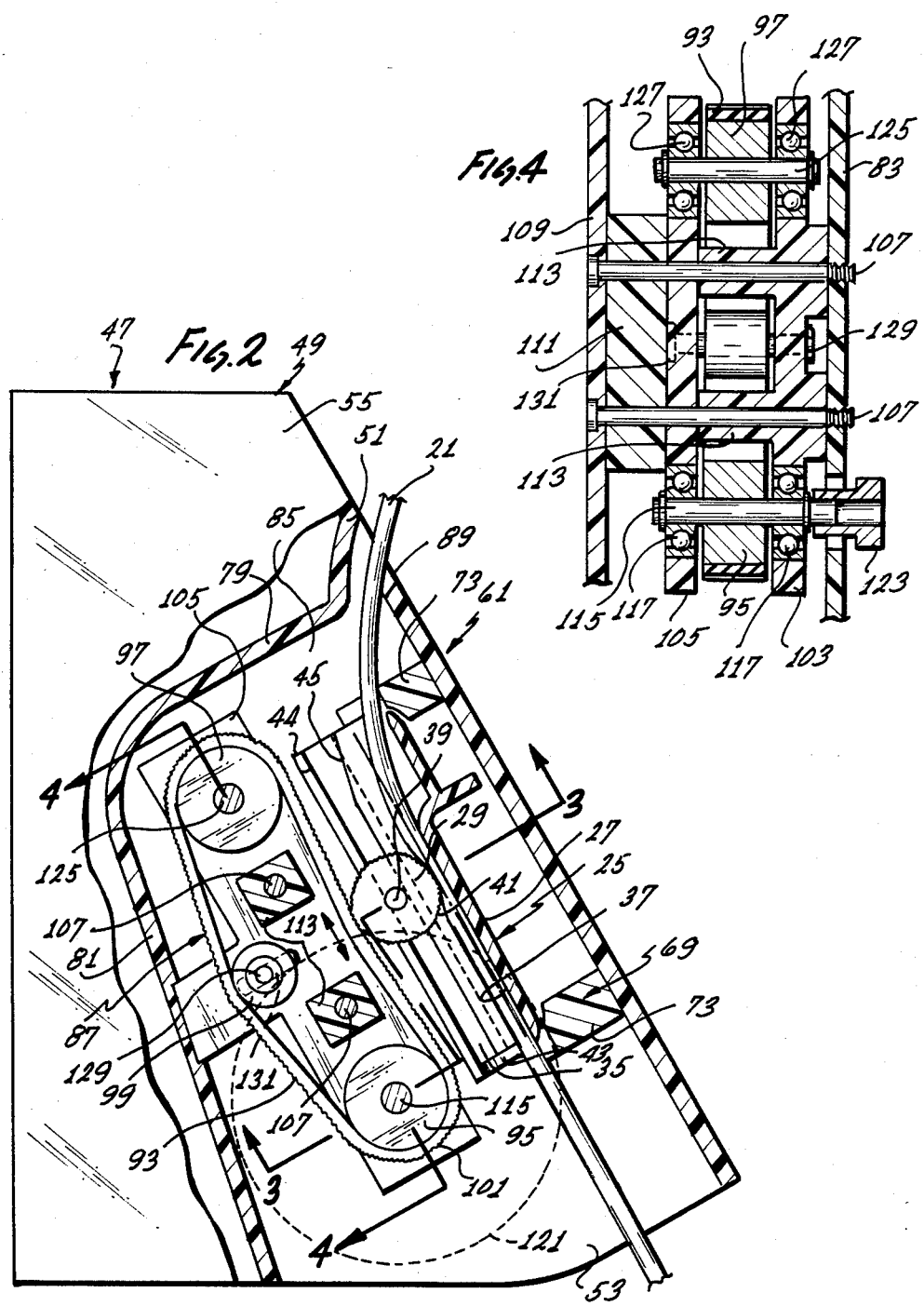

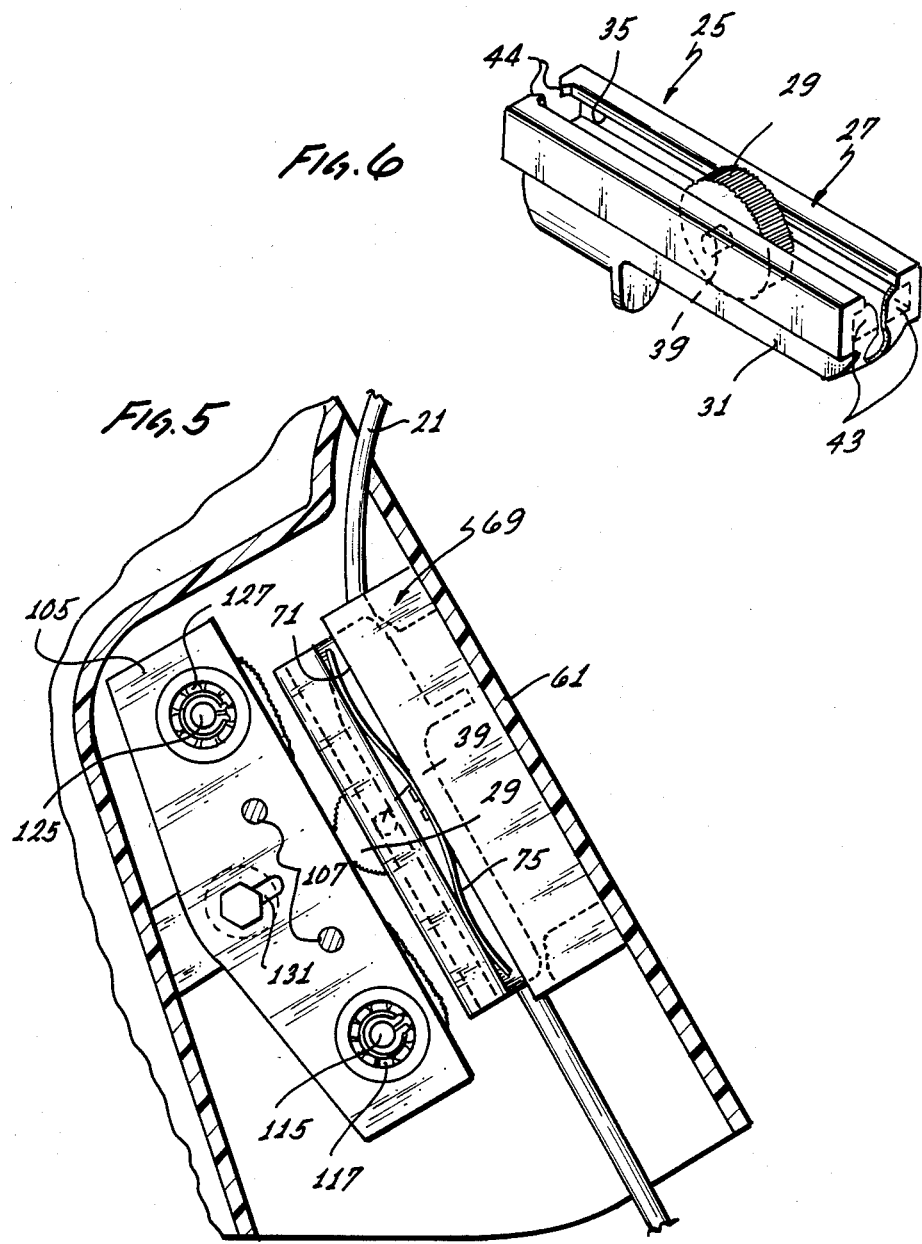

4,553,963

ROLLER CLAMP CONTROLLER

BACKGROUND OF THE INVENTION

Various medical procedures require the administration of liquids, such as parenteral fluids, blood and enteral products, to a patient. These fluids are typically administered to the patient under gravity flow. For example, an IV (intravenous) administration set comprising a source of the fluid, a flexible conduit and a valve may be used to administer these fluids.

One commonly used valve is a roller clamp. A roller clamp includes a body, a rotary or control member mounted on the body for rotation and translation relative to the body and a ramp on the body. The flexible conduit is received between the rotary member and the ramp. Accordingly, by rotating the rotary member, the rotary member translates along the ramp to selectively restrict the conduit to control the flow of fluid through the conduit to the patient.

The roller clamp is manually controlled. However, it is known to control a particular valve of unique construction with a stepper motor, and one such apparatus is disclosed in Cannon U.S. Pat. No. 4,300,552. This patented apparatus cannot be used to drive the roller clamp described above. Other automatic control apparati that also cannot be used to drive a roller clamp are shown in Lamadrid U.S. Pat. No. 4,397,642 and Sadlier et al U.S. Pat. No. 4,105,028.

SUMMARY OF THE INVENTION

This invention provides a controller for controlling a roller clamp of the type described above. The controller is motor driven and automatically controls the position of the roller clamp and the flow of fluid to the patient. Thus, with this invention, the conventional roller clamp which is in common use can be controlled, and there is no need to provide a valve of special, unique construction. Accordingly, the cost of the disposable administration set is not increased. Although the controller of this invention is particularly adapted for controlling a roller clamp, the invention is also applicable to controlling other valves.

The controller includes means for retaining the roller clamp, and preferably such means includes a supporting structure and means for mounting the roller clamp on the supporting structure. The roller clamp is driven by drive means, which is preferably mounted on the supporting structure. The drive means is drivingly engageable with the rotary member of the roller clamp for rotating the rotary member while allowing the rotary member to translate to selectively restrict the conduit and to control the flow of fluid through the conduit to the patient. The motor is preferably automatically controlled by a motor controller.

The rotary member translates along the ramp as it rotates. The drive means of this invention rotates the rotary member and does not interfere with the concomitant translation of the rotary member. Although various drive means which embody this concept can be utilized, the preferred drive means includes a belt drivingly engageable with the rotary member of the valve. Of those drives which embody this concept, a belt drive is preferred because it is compact and relatively inexpensive. In a preferred construction, the belt is an endless belt which is mounted on at least two pulleys.

In order that the motor can accurately control the flow of fluid to the patient, it is necessary that a predetermined movement of the motor equal a known movement of the rotary member of the roller clamp. To achieve this, it is important that there be essentially no slippage between the belt and the rotary member and that the belt undergo essentially no elongation. In a preferred construction, high friction between the roller clamp and the belt is provided by constructing at least the driving face of the belt of a soft high-friction plastic material, such as urethane, and by providing the driving face with an irregular surface, such as a series of resilient teeth. These teeth are sized and arranged to mesh with knurling on the periphery of the rotary member. To minimize elongation of the belt, it preferably comprises fibers, such as woven nylon, in a polymeric matrix with the fibers arranged to minimize elongation of the belt.

The supporting structure may include a movable support member on which the roller clamp can be mounted. The movable support member is movable between a loading position in which the drive means is out of driving engagement with the rotary member and a driving position in which the drive means is in driving engagement with the rotary member. In the loading position, the roller clamp can be easily loaded or mounted on the movable support member. In one preferred construction, the movable support member is in the form of a pivotable door.

In the driving position, resilient means is used to hold the rotary member against the drive means, and the resilient means may be used to bias the rotary member into engagement with the drive means. For this purpose, the roller clamp is movably mounted on a member of the supporting structure and a spring acts between the supporting structure and the roller clamp to urge the rotary member against the drive means.

The invention, together with additional features and advantages thereof, may best be understood by reference to the following description taken in connection with the accompanying illustrative drawing.

BRIEF DESCRIPTION OF THE DRAWING

FIG. 1 is a partially schematic and partially perspective view illustrating an apparatus for administering a fluid to a patient.

FIG. 2 is an enlarged elevational view partially in section taken generally along line 2—2 of FIG. 1.

FIG. 3 is a fragmentary sectional view taken generally along line 3—3 of FIGS. 1 and 2.

FIG. 4 is a fragmentary sectional view taken generally along line 4—4 of FIG. 2.

FIG. 5 is a view similar to FIG. 2 with the drive means, roller clamp and retainer for the roller clamp shown in side elevation.

FIG. 6 is an isometric view of a roller clamp.

DESCRIPTION OF THE PREFERRED EMBODIMENT

FIG. 1 shows an apparatus 11 for gravity administration of a fluid to a patient 13 through an IV set 15, which may be of conventional design. The IV set 15 includes a source 17 of parenteral fluid, a drip chamber 19, a clear, flexible, plastic tube 21 coupled to the distal end of the drip chamber, a needle 23 coupled to the distal end of the tube 21 and received within a vein of the patient 13 and a valve in the form of a roller clamp 25 (FIGS. 2 and 3). The proximal end of the drip chamber 19 is coupled, either directly or through a tube or other conventional IV set elements, to the source 17. Accordingly, a conduit is provided leading from the source 17 to the patient 13.

The roller clamp 25 controls the flow of the fluid through the tube 21 to the patient 13. The roller clamp 25, which is of conventional construction, comprises a body 27 (FIGS. 2 and 3) and a rotary member or roller 29. The body 25 is somewhat channel shaped and includes opposed side walls 31 integrally joined by an end wall 33. The side walls 31 have opposed grooves 35. The inner surface of the end wall 33 is inclined slightly toward the grooves 35 as it extends downwardly as viewed in FIG. 2 to define a ramp 37. The roller clamp 25 is preferably constructed of a rigid plastic material.

The rotary member 29 is mounted for rotation and translation on, and relative to, the body 27 by stub shafts 39 coaxially mounted on the rotary member 29 and received within the grooves 35, respectively. The rotary member 29 has a peripheral surface 41 which has been knurled to define a series of miniature teeth extending axially of the rotary member. The grooves 35 terminate in shoulders 43 and 44 (FIG. 2) which limit the travel of the rotary member. At one end, each of the grooves 35 has a widened portion 45 to facilitate entry of the stub shafts 39 into the grooves, respectively.

With this construction, the tube 21 can be received by the roller clamp 25 between the rotary member 29 and the ramp 37 with the tube lying along the ramp. The opposite ends of the body 27 are open as shown in FIG. 2 to permit the tube 21 to pass completely through the body 27. As best shown in FIG. 2, a region of the tube 21 is resiliently compressed between the rotary member 29 and the adjacent region of the ramp 37. By rotating the rotary member 29 counterclockwise as viewed in FIG. 2, the rotary member, by virtue of its engagement with the tube 21, translates generally downwardly (as viewed in FIG. 2) relative to the body 27 and the tube 21. Because the ramp 37 is inclined toward the grooves 35, which define the path of travel of the rotary member 29, the tube is progressively further restricted, and the flow of fluid through the tube is correspondingly diminished. Conversely, to increase the flow through the tube 21, the rotary member 29 is rotated clockwise as viewed in FIG. 2 to cause the rotary member to translate generally upwardly as viewed in FIG. 2.

The apparatus 11 includes a controller 47 (FIG. 1) which is particularly adapted for automatically controlling the flow of fluid through the tube 21 by appropriately rotating the rotary member 29. In the illustrated embodiment, the controller 47 includes a supporting structure in the form of a housing 49 which forms an essentially complete enclosure and which has a front wall 51, an opening 53 in a bottom wall (FIG. 2) and a side wall 55 forming portions of that enclosure. The front wall 51 comprises a fixed panel 59 (FIG. 3) and a movable support member in the form of a door 61 suitably, pivotally attached to the fixed panel 59 as by a pin 63 (FIG. 3). The door 61 is pivotable between a closed or driving position shown in FIG. 3 in which the panel 59 and the door 61 are essentially coplanar and an open or loading position in which the door 61 is pivoted clockwise, e.g., 90 degrees, from the position shown in FIG. 3 for purposes described more fully hereinbelow. The door 61 is normally held in the driving position by a latch 64 suitably pivotally mounted on the outer end of the door 61 as by a pin and socket joint 65 and a hook 66 on the wall 55 which engages the end of the latch remote from the door. A leaf spring 67 is attached to the door 61 and engages the latch 64 to bias it clockwise into locking engagement with the hook 66 and to take up tolerances in the door 61 and the pin 63.

The door 61 includes means for mounting the roller clamp 25 on the housing 49. Such means includes a retainer 69 mounted on the inner side of the door 61. Although various constructions are possible, the retainer 69 can advantageously include side walls 71 (FIG. 3) and end walls 73 (FIG. 2) for receiving, and frictionally mounting, the roller clamp 25. Leaf springs 75 (FIGS. 3 and 5) act between the side walls 71 and the body 27 to bias the roller clamp 25 away from the door 61.

The housing 49 includes interior partitions 79, 81, and 83 which cooperate with regions of the front wall 51 and side wall 55 to define a compartment 85 having an open bottom for housing the roller clamp 25 and drive means 87 for the roller clamp. The door 61 provides access to the compartment 85, and an opening 89 (FIG. 2) in the front wall 51 allows the tube 21 to pass through the compartment.

In the illustrated embodiment of the invention, the drive means 87 includes an endless belt 93 mounted on a driving pulley 95, a driven pulley 97 and a tensioning roller or pulley 99. The belt 93 is preferably constructed of cast urethane with a woven nylon reinforcement oriented so as to minimize elongation of the belt. The belt 93 may be constructed, for example, by placing the woven nylon reinforcement in a mold and casting the urethane around the reinforcement to capture it. The belt 93 has an outer driving face comprising a series of resilient teeth 101 which are sized and arranged to mesh with the teeth on the peripheral surface 41 of the rotary member 29.

Although the pulleys 95, 97 and 99 can be mounted for rotation in different ways, in the embodiment illustrated, they are mounted on the partition 83 by bearing blocks 103 and 105 and bolts 107 as best shown in FIG. 4. More specifically, the bolts 107 extend through a section 109 (FIGS. 3 and 4) of the side wall 55, a block 111 and the bearing blocks 103 and 105 into the partition 83. The bearing block 103 has integral, tubular sections 113 for separating the bearing blocks 103 and 105.

The driving roller 95 is mounted for rotational movement with a shaft 115 which is mounted for rotation within bearings 117 carried by the bearing blocks 103 and 105, respectively. The shaft 115 is coupled to an output shaft 119 of a motor 121, such as an electric motor, by a coupling 123 which extends through an opening 124 in the partition 83 as shown in FIG. 3. Although the motor 121 could be a servo motor, it is preferably a stepper motor.

The driven pulley 97 is mounted for rotation with a shaft 125 which is rotatably mounted within bearings 127 carried by the bearing blocks 103 and 105, respectively. The tensioning pulley 99 is rotatably mounted on a shaft 129 which extends through aligned slots 131 in the bearing blocks 103 and 105 and has its opposite ends releasably affixed to the bearing blocks. The tension on the belt 93 can be adjusted by adjusting the position of the shaft 129 along the slot 131.

The motor 121 can be controlled in different ways. For example, the controller 47 may include an input terminal 133 (FIG. 1) within the housing 49, and the terminal may include a keyboard for inputting flow rate information which may be the flow rate of the liquid from the source 17 to the patient 13 or information from which the desired flow rate can be calculated. The actual flow rate can be calculated by a flow rate calculator 134 which processes signals from a drop sensor 135 of conventional construction which detects the drops passing through the drip chamber 19. Signals representing the desired flow rate from the input terminal 133 and the actual flow rate from the flow rate calculator 134 are fed to a comparator 137 which compares these two signals and produces an error signal representing the difference between the signals from the input terminal and the drop sensor. This error signal is then introduced into the motor 121 which drives the drive means 87 and the rotary member 29 in a direction and in approximately the correct amount to eliminate the error. Alternatively, the motor 121 can be controlled by a suitable microprocessor circuit.

In use, the door 61 is moved to the open or loading position, and the roller clamp 25 is positioned in the retainer 69. The door 61 is then moved to the closed or driving position to bring the rotary member 29 into driving engagement with the belt 93 as shown in FIGS. 2 and 3. In this position, the belt 93 drivingly engages the rotary member 29 so that movement of the belt rotates the rotary member 29 and causes it to translate along the grooves 35 and the ramp 37. The leaf springs 75 bias the rotary member 29 toward the belt 93. In the open or loading position, the rotary member 29 is out of driving engagement with the belt 93.

With the desired flow rate entered into the comparator 137 from the input terminal 133, the motor 121 drives the belt 93 to move the rotary member 29 toward the full open position, and when flow is sensed by the drop sensor 135, the motor 121 is reversed by an amount reasonably calculated to establish the desired flow rate. This process of comparing desired and actual flow rates and adjusting the motor 121 accordingly is repeated until the flow rate is within the established tolerances of the rate demanded by the input terminal 133. Sensors (not shown), such as a light source and photocell, which perform a limit-switch function can be used to sense the limits of travel of the rotary member 29 in the grooves 35. Although the apparatus 11 is particularly adapted for continuing operation, if the roller clamp 25 is removed from the controller 47, the roller clamp 25 is set to the desired flow rate, and no appreciable change in the flow rate occurs.

Although an exemplary embodiment of the invention has been shown and described, many changes, modifications and substitutions may be made by one having ordinary skill in the art without necessarily departing from the spirit and scope of this invention.

I claim:

1. A controller for controlling the flow of fluid through a conduit from a source to a patient wherein the conduit has a flexible wall portion and a roller clamp having a body, a rotary member which is mounted on the body for rotation and translation, and a ramp receives the flexible wall portion between the rotary member and the ramp and wherein the rotary member is rotatable and translatable to restrict the conduit at said flexible wall portion a selected amount to control the flow of fluid through the conduit, said controller comprising:
   a supporting structure;
   means for mounting the roller clamp on the supporting structure;
   drive means on the supporting structure drivingly engageable with the rotary member of the roller clamp when the roller clamp is mounted on the supporting structure by said mounting means for rotating the rotary member while allowing the rotary member to translate to selectively restrict the conduit at the flexible wall portion; and
   motor means for driving the drive means.

2. A controller as defined in claim 1 wherein said supporting structure includes a movable member and said mounting means mounts the roller clamp on the movable member, said supporting structure includes means for mounting the movable member for movement between a first position in which the drive means is out of driving engagement with the rotary member and a second position in which the drive means is in driving engagement with the rotary member.

3. A controller as defined in claim 2 wherein the mounting means for the movable member mounts the movable member for pivotable movement between said first and second positions.

4. A controller as defined in claim 2 wherein said drive means includes an endless drive belt engageable with the rotary member when the rotary member is mounted on the supporting structure to drive the rotary member.

5. A controller as defined in claim 1 wherein said drive means includes an elongated drive element engageable with the rotary member when the rotary member is mounted on the supporting structure to drive the rotary member.

6. A controller as defined in claim 5 wherein said drive element includes a drive belt.

7. A controller as defined in claim 6 wherein said belt comprises a plurality of fibers in a polymeric matrix arranged to minimize elongation of the belt.

8. A controller as defined in claim 1 wherein said mounting means includes resilient means for use in holding the rotary member against the drive means.

9. A controller for controlling the flow of fluid through a conduit from a source to a patient wherein a valve has a movable control member which is movable to selectively restrict flow through the conduit to the patient, said controller comprising:
   a supporting structure;
   means for mounting the valve on the supporting structure;
   an endless belt;
   first and second pulleys mounted for rotation on the supporting structure, said belt being mounted on said pulleys and being drivingly engageable with the control member of the valve when the valve is mounted on the supporting structure by said mounting means for driving the control member to selectively restrict flow through the conduit to the patient; and
   motor means for driving the belt.

10. A controller as defined in claim 9 wherein said supporting structure includes a movable support member and said mounting means mounts the valve on the movable support member, said supporting structure includes means for mounting the movable support member for movement between a first position in which the belt is out of driving engagement with the control member and a second position in which the belt is in driving engagement with the control member.

11. A controller as defined in claim 10 wherein the mounting means for the movable support member mounts the movable support member for pivotable movement between said first and second positions.

12. A controller as defined in claim 9 wherein said belt comprises a plurality of fibers in a polymeric matrix arranged to minimize elongation of the belt.

13. A controller as defined in claim 9 wherein said belt has an irregular driving surface which is engageable with the control member.

14. A controller as defined in claim 9 including a motor controller for controlling the motor and means for inputting to said motor controller flow rate information whereby the motor controller can control the motor and the motor can control the valve to provide a desired flow rate.

15. A controller as defined in claim 9 wherein said belt has a driving face for driving the control member of the valve and said driving face comprises a series of resilient teeth.

16. An apparatus for administering a fluid from a source to a patient comprising:
a conduit adapted to extend from the source to the patient, said conduit having a flexible wall portion;
a roller clamp including a body, a rotary member, means for mounting the rotary member on the body for rotation and translation relative to the body, and a ramp on said body, said flexible wall portion of said conduit being received by the roller clamp between the rotary member and the ramp whereby the rotary member is rotatable to translate the rotary member along the ramp to restrict the conduit at the flexible wall portion a selected amount to thereby control the flow of the fluid through the conduit to the patient;
means for retaining the roller clamp;
drive means engageable with the rotary member of the roller clamp when the roller clamp is retained by the retaining means for rotating the rotary member to translate the rotary member along the ramp to selectively restrict the conduit at the flexible wall portion; and
motor means for driving the rotary member.

17. An apparatus as defined in claim 16 wherein said drive means includes an elongated drive element engageable with the rotary member when the roller clamp is retained by the retaining means.

18. An apparatus as defined in claim 17 wherein said drive element includes an endless drive belt.

19. An apparatus as defined in claim 18 wherein said drive belt has a drive surface engageable with the rotary member to drive the rotary member and said drive surface and said rotary member have cooperating teeth which are drivingly engageable.

20. An apparatus as defined in claim 16 wherein said retaining means includes means for moving the roller clamp to selectively place the rotary member into and out of driving engagement with the drive means.

* * * * *